United States Patent
Liu et al.

(10) Patent No.: US 11,702,439 B2
(45) Date of Patent: Jul. 18, 2023

(54) METHOD FOR PREPARING TRIFLURIDINE

(71) Applicant: CHIA TAI TIANQING PHARMACEUTICAL GROUP CO., LTD., Jiangsu (CN)

(72) Inventors: Lin Liu, Jiangsu (CN); Rui Zhao, Jiangsu (CN); Guangming Sang, Jiangsu (CN); Xingjian Zhou, Jiangsu (CN); Xiaopeng Guo, Jiangsu (CN); Aiming Zhang, Jiangsu (CN); Gang Wu, Jiangsu (CN); Chunguang Xia, Jiangsu (CN); Xiquan Zhang, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 209 days.

(21) Appl. No.: 17/262,186

(22) PCT Filed: Jul. 24, 2019

(86) PCT No.: PCT/CN2019/097439
§ 371 (c)(1),
(2) Date: Jan. 21, 2021

(87) PCT Pub. No.: WO2020/020208
PCT Pub. Date: Jan. 30, 2020

(65) Prior Publication Data
US 2021/0292356 A1    Sep. 23, 2021

(30) Foreign Application Priority Data
Jul. 24, 2018   (CN) .......................... 201810817373.6

(51) Int. Cl.
*C07H 19/06* (2006.01)
(52) U.S. Cl.
CPC ................... *C07H 19/06* (2013.01)

(58) Field of Classification Search
None
See application file for complete search history.

(56) References Cited

U.S. PATENT DOCUMENTS

| 5,006,646 A | 4/1991 | Itoh et al. |
| 6,423,852 B1 | 7/2002 | Umetani |

FOREIGN PATENT DOCUMENTS

| CN | 1366530 A | 8/2002 |
| CN | 100334100 C | 8/2007 |
| CN | 103130855 A | 6/2013 |
| CN | 105461772 A | 4/2016 |
| CN | 106220699 A | 12/2016 |
| CN | 109021048 A | 12/2018 |
| EP | 1 176 150 A1 | 1/2002 |
| WO | 2019049174 A1 | 3/2019 |

OTHER PUBLICATIONS

Extended European Search Report dated Mar. 18, 2022 as received in application No. 19841191.0.
Komatsu, Umetani: "Synthesis of Trifluorothymidine: Green Glycosylation Condition Using Neither Chloroform nor Transition Metals", Organic Process Research and Development, vol. 6, No. 6, 2002, pp. 847-850, xP002232523, DOI: 10.1021/0P0255550 * p. 849, scheme 3 and paragraph bridging pp. 849 and 850.
Chinese Office Action dated Sep. 18, 2021 as received in application No. 201980047151.3.
Ryan et al., Chemical Synthesis of 2'-Deoxy-5-(trifluoromethyl)uridine and the a Anomer, Life Sciences Research, Stanford Research Institute, Menlo Park, California. Nov. 10, 1966.

*Primary Examiner* — Patrick T Lewis
(74) *Attorney, Agent, or Firm* — Maschoff Brennan

(57) ABSTRACT

The present application relates to a method for preparing trifluridine, comprising reacting a compound of formula III with a compound of formula IV in a first solvent in the presence of an acid to obtain a compound of formula II, and performing further reaction to obtain trifluridine.

19 Claims, No Drawings

METHOD FOR PREPARING TRIFLURIDINE

CROSS-REFERENCE TO RELATED APPLICATIONS

This application claims the benefit of the Chinese patent application No. 201810817373.6 filed with the State Intellectual Property Office of China on Jul. 24, 2018. The disclosure of the application is herein incorporated by reference in its entirety.

FIELD OF THE INVENTION

The present application relates to the fields of organic chemistry and medicinal chemistry. Specifically, it relates to a method for preparing trifluridine.

BACKGROUND OF THE INVENTION

Trifluridine, with molecular formula: $C_{10}H_{11}F_3N_2O_5$, molecular weight: 296.2, full name: 1-(2-deoxy-β-D-erythrofuranose)-5-trifluoromethyl-2,4-dihydroxypyrimidine, English name: Trifluridine, and its chemical structure is as follows:

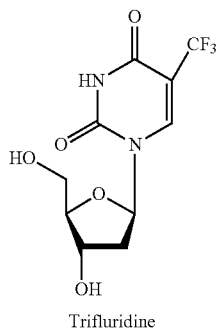

Trifluridine

Trifluridine has the strongest effect on herpes simplex virus (HSV-1 and HSV-2), and it also has a certain effect on adenovirus, vaccinia virus, cytomegalovirus, and herpes zoster virus. To acyclovir-resistant herpes virus, it works. Its triphosphate derivatives can bind to DNA and competitively inhibit DNA polymerase with thymidine triphosphate. No selectivity is shown to viral DNA and host cell DNA. And it is suitable for herpes simplex keratitis, conjunctivitis and other herpetic eye diseases.

In the synthesis process of trifluridine, the key intermediates (that is, compound of formula II) exist in two configurations, α and R, and the preparation of formula II compound with high R/α ratio is a technical problem that needs to be solved during the preparation.

Patent document CN1366530A discloses a preparation method for improving the selectivity of trifluridine intermediate β, but it is difficult to be applied in industrial production. Firstly, the pure α-configuration ribose raw material shown in formula (2) used in this method is difficult to obtain on the market, and it is easy buy the raw materials with α/β mixed configuration. Secondly, the literature suggests that there is solvent-free or low-solvent reaction, in which the solvent-free reaction is not suitable for industrial production, and there is a problem that the reaction system is viscous and difficult to stir when solvent is low.

Formula II

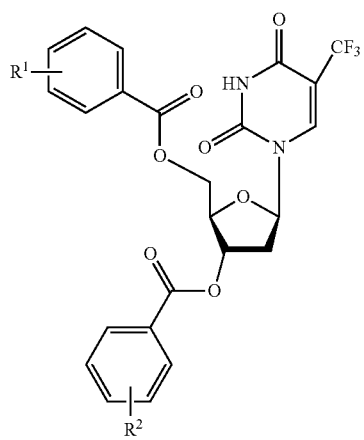

Formula (2)

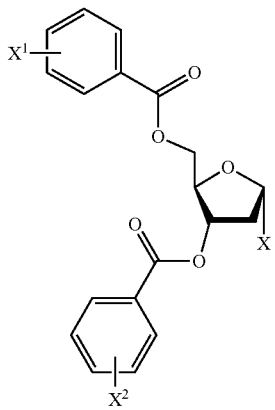

Therefore, it is still an urgent problem to be solved in the art to further look for a preparation method of trifluridine which is more suitable for industrial production.

DETAILED DESCRIPTION OF THE INVENTION

In one aspect, the present application provides a method for preparing a compound of formula II, wherein a compound of formula III and a compound of formula IV are reacted in a first solvent in the presence of an acid to obtain the compound of formula II,

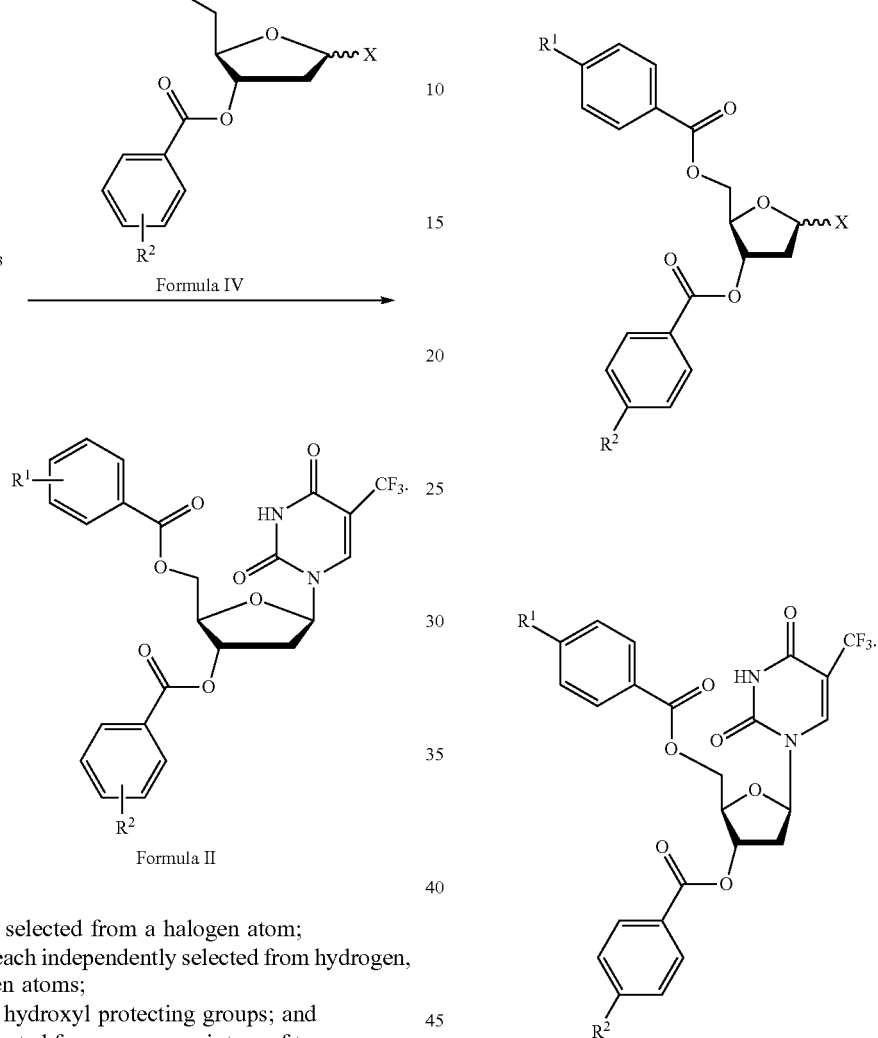

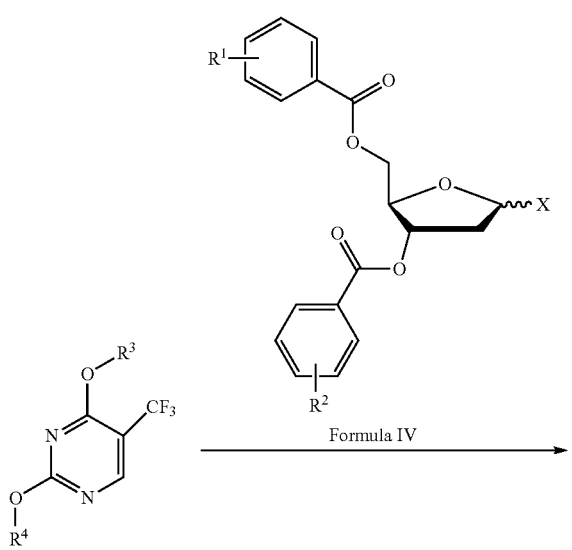

Wherein, X is selected from a halogen atom;

R¹ and R² are each independently selected from hydrogen, methyl or halogen atoms;

R³ and R⁴ are hydroxyl protecting groups; and

The acid is selected from one or a mixture of two or more of HCl, formic acid, acetic acid or acetic anhydride.

In some embodiments of the present application, X is selected from chlorine or bromine.

In some embodiments of the present application, X is selected from chlorine.

In some embodiments of the present application, R¹ and R² are each independently selected from fluorine, chlorine, bromine or iodine.

In some embodiments of the present application, R¹ and R² are each independently selected from chlorine or bromine.

In some embodiments of the present application, R¹ and R² are both chlorine.

In some embodiments of the present application, R³ and R⁴ are each independently selected from TMS, TBDPS, TBDMS or TIPS.

In some embodiments of the present application, R³ and R⁴ are each independently selected from TMS or TBDMS.

In some embodiments of the present application, R³ and R⁴ are both TMS.

In some embodiments of the present application, the compound of formula IV has a structure shown by formula IV-A, and the compound of formula II has a structure shown by formula II-A:

In some embodiments of the present application, the compound of formula IV has a structure shown by formula IV-1, the compound of formula III has a structure shown by formula III-1, and the compound of formula II has a structure shown by formula II-1:

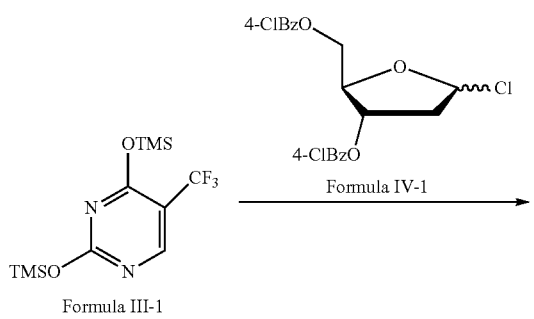

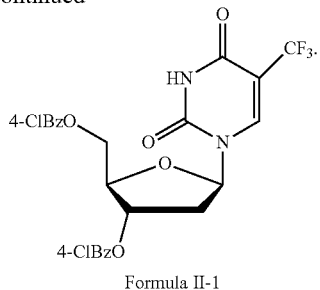

Formula II-1

In some embodiments of the present application, the molar ratio of the compound of formula III to the compound of formula IV is 1:1 to 1:3. In some embodiments of the present application, the molar ratio of the compound of formula III to the compound of formula IV is 1:1 to 1:2. In some embodiments of the present application, the molar ratio of the compound of formula III to the compound of formula IV is 1:1 to 1:1.5. In some embodiments of the present application, the molar ratio of the compound of formula III to the compound of formula IV is 1:1.1 to 1:1.2. In some embodiments of the present application, the molar ratio of the compound of formula III to the compound of formula IV is 1:1.15.

In some embodiments of the present application, the acid is selected from one or a mixture of two or more of an alcohol solution of hydrogen chloride, formic acid, acetic acid or acetic anhydride. In some embodiments of the present application, the acid is selected from one or a mixture of two or more of a methanol solution of hydrogen chloride, an ethanol solution of hydrogen chloride, an isopropanol solution of hydrogen chloride, a tert-butanol solution of hydrogen chloride, acetic acid or acetic anhydride. In some embodiments of the present application, the acid is selected from one or a mixture of two or more of an isopropanol solution of hydrogen chloride, acetic acid or acetic anhydride. In some embodiments of the present application, the acid is acetic anhydride.

In some embodiments of the present application, the concentration of the alcohol solution of hydrogen chloride is 3 mol/L to 10 mol/L. In some embodiments of the present application, the concentration of the alcohol solution of hydrogen chloride is 4 mol/L to 8 mol/L. In some embodiments of the present application, the concentration of the alcohol solution of hydrogen chloride is 5 mol/L to 7 mol/L. In some embodiments of the present application, the concentration of the alcohol solution of hydrogen chloride is 6 mol/L. In some embodiments of the present application, the alcohol solution of hydrogen chloride is an isopropanol solution with 6 mol/L hydrogen chloride.

In some embodiments of the present application, the molar ratio of the acid to the compound of formula III is 0.05:1 to 0.3:1. In some embodiments of the present application, the molar ratio of the acid to the compound of formula III is 0.1:1 to 0.25:1. In some embodiments of the present application, the molar ratio of the acid to the compound of formula III is 0.15:1 to 0.2:1. In some embodiments of the present application, the molar ratio of the acid to the compound of formula III is 0.2:1.

In some embodiments of the present application, in the above preparation method, the first solvent is selected from one or a mixture of two or more of 1,2,4-trichlorobenzene, o-dichlorobenzene, chlorobenezene, anisole, toluen, nitrobenzene, isopropyl alcohol, ether, tetrahydrofuran, and ethyl acetate. In some embodiments of the present application, the first solvent is selected from one or a mixture of two or more of 1,2,4-trichlorobenzene, o-dichlorobenzene, chlo-robenzene, anisole, toluene, nitrobenzene and isopropyl alcohol. In some embodiments of the present application, the first solvent is selected from one or a mixture of two or more of anisole, toluene and isopropyl alcohol. In some embodiments of the present application, the first solvent is selected from one or a mixture of two of anisole and toluene. In some embodiments of the present application, the first solvent is anisole.

In some embodiments of the present application, the ratio of the mass of the first solvent to the mass of the compound of formula III is 0.35:1 to 0.77:1. In some embodiments of the present application, the ratio of the mass of the first solvent to the mass of the compound of formula III is 0.35:1 to 0.55:1. In some embodiments of the present application, the ratio of the mass of the first solvent to the mass of the compound of formula III is 0.40:1 to 0.45:1. In some embodiments of the present application, the ratio of the mass of the first solvent to the mass of the compound of formula III is 0.42:1.

In some embodiments of the present application, the temperature of the above reaction is 20° C. to 70° C. In some embodiments of the present application, the reaction temperature is 40° C. to 60° C. In some embodiments of the present application, the reaction temperature is 40° C. to 50° C.

In some embodiments of the present application, the reaction time of the above reaction is 1 h to 8 h. In some embodiments of the present application, the reaction time is 2 h to 5 h. In some embodiments of the present application, the reaction time is 2 h to 3 h.

In some embodiments of the present application, in the compound of formula IV, the ratio of α configuration/β configuration is 3 to 0.7:1. In some embodiments of the present application, in the compound of formula IV, the ratio of α configuration/β configuration is 2 to 0.85:1. In some embodiments of the present application, in the compound of formula IV, the ratio of α configuration/β configuration is 1 to 1.7:1.

In some embodiments of the present application, the above preparation method further comprises: adding solvent B to the reaction system which contains the compound of formula II after reacting, and cooling for crystallization to obtain a preliminarily purified compound of formula II.

In some embodiments of the present application, the solvent B is one or two or more mixed solvents selected from ethanol, isopropanol, and n-propanol. In some embodiments of the present application, the solvent B is one or two mixture of ethanol and isopropanol. In some embodiments of the present application, the solvent B is ethanol, such as absolute ethanol.

In some embodiments of the present application, the ratio of the mass of the solvent B to the mass of the compound of formula III is 1.5 to 4:1. In some embodiments of the present application, the ratio of the mass of the solvent B to the mass of the compound of formula III is 2 to 3:1. In some embodiments of the present application, the ratio of the mass of the solvent B to the mass of the compound of formula III is 2 to 2.5:1. In some embodiments of the present application, the ratio of the mass of the solvent B to the mass of the compound of formula III is 2.37:1.

In some embodiments of the present application, the crystallization temperature is −5° C. to 40° C. In some embodiments of the present application, the crystallization temperature is −5° C. to 10° C. In some embodiments of the present application, the crystallization temperature is −5° C. to 5° C.

In some embodiments of the present application, the crystallization time is 1 h to 15 h. In some embodiments of the present application, the crystallization time is 3 h to 12 h. In some embodiments of the present application, the crystallization time is 7 h to 10 h.

On the other hand, the above-mentioned preparation method of the present application also includes a purification step of the compound of formula II. Wherein this method includes dissolving the above-mentioned compound of formula II purified preliminarily in a solvent D, and cooling for crystallization to obtain a refined product of the compound of formula II. Wherein, preferably, the solvent D is selected from one or two or more mixed solvents of ethanol, isopropanol, and n-propanol.

In some embodiments of the present application, the solvent D is selected from one or two mixture of ethanol and isopropanol. In some embodiments of the present application, the solvent D is ethanol.

In some embodiments of the present application, the ratio of the mass of the solvent D to the mass of the compound of formula II purified preliminarily is 7.9:1 to 20:1. In some embodiments of the present application, the ratio of the mass of the solvent D to the mass of the compound of formula II purified preliminarily is 10:1 to 15:1. In some embodiments of the present application, the ratio of the mass of the solvent D to the mass of the compound of formula II purified preliminarily is 13:1 to 15:1. In some embodiments of the present application, the ratio of the mass of the solvent D to the mass of the compound of formula II purified preliminarily is 14:1.

In some embodiments of the present application, the above-mentioned crystallization temperature is −10° C. to 50° C. In some embodiments of the present application, the above-mentioned crystallization temperature is 0° C. to 35° C. In some embodiments of the present application, the above-mentioned crystallization temperature is 20° C. to 25° C.

In some embodiments of the present application, there is provided a method for preparing trifluridine using the compound of formula II obtained above. The method comprises obtaining the compound of formula II according to the above preparation method; dissolving the compound of formula II in anhydrous methanol to obtain its anhydrous methanol solution; adding a methanol solution of sodium methoxide to the anhydrous methanol solution for reacting to obtain trifluridine:

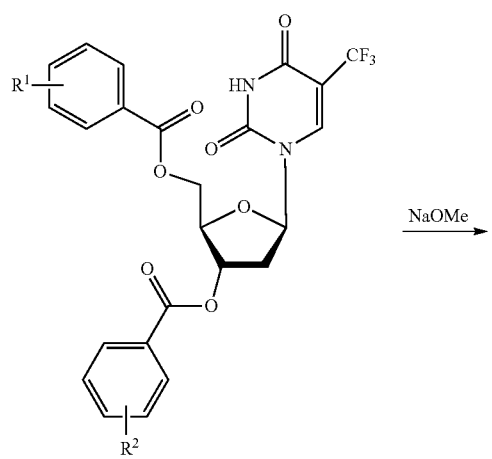

Formula II

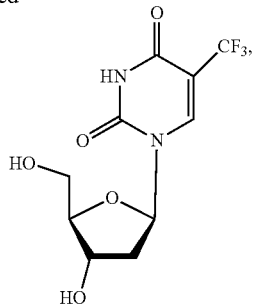

Formula I

Wherein, the definitions of $R^1$ and $R^2$ are as described above.

In the present application, "adding a solvent or a reactant" includes adding the solvent or reactant at once or in batches.

In the present application, "h" means hours.

In the present application, "kg" means kilograms.

In the present application, "4-ClBz" means 4-chlorobenzoyl.

In the present application, "TMS" means trimethylsilyl.

In the present application, "TBDPS" means tert-butyldiphenylsilyl.

In the present application, TBDMS" means tert-butyldimethylsilyl.

In the present application, "TIPS" means triisopropylsilyl.

In the present application, "HMDS" means hexamethyldisilazane.

In the present application, "eq" means equivalent. For example, "acid/compound of formula III (eq)" means a molar ratio of acid to compound of formula III.

In the present application, "pre-dried" refers to the solvent that has been dried over 4A molecular sieve before being put into the reaction. The amount of the molecular sieve is a conventional amount in the technical field.

In the present application, the structural formula of β configuration of the compound of formula IV is

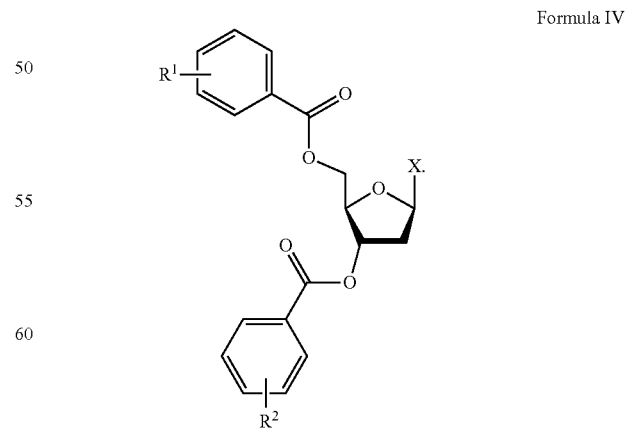

Formula IV

In the present application, the structural formula of α configuration of the compound of formula IV is

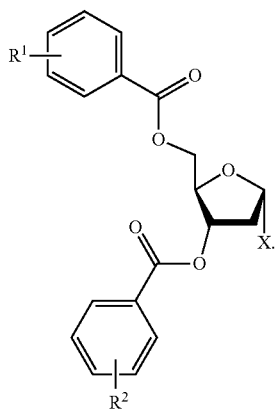

Formula IV

In the present application, the compound of formula II is in the β configuration, and the structural formula of the corresponding α configuration is

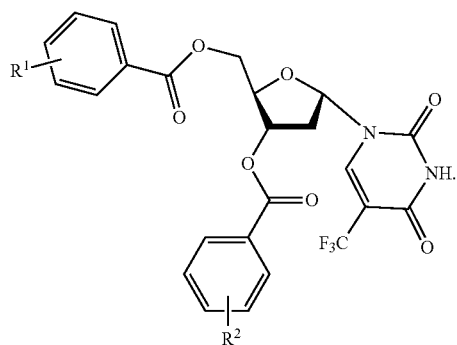

In the present application, in the compound of formula II, the ratio of α configuration and β configuration is determined by HPLC. The specific test conditions of HPLC are as follows:

Instrument model: Shimadzu High Performance Liquid Chromatograph SPD-20A LC-20AD Column: Thermo BDS C18 (4.6 mm×25 cm, 5 μm)

Mobile phase A: 10 mM potassium dihydrogen phosphate solution, Mobile phase B: acetonitrile A/B (V/V=40/60) isocratic elution for 50 min Column temperature: 30° C.; Flow rate: 1.0 mL/min; Detection wavelength: 240 nm; Sample concentration: 1 mg/mL; Injection volume: 10 μL; Solvent: acetonitrile.

Record the chromatogram to 60 min, and the retention time of α configuration to β configuration of the compound of formula II-1 is about 0.88 (wherein, the retention time of β isomer of the compound of formula II-1 is 15.645 min; the retention time of α isomer of the compound of formula II-1 is 13.743 min).

In the present application, unless otherwise specified, the ratio of "α:β" refers to the molar ratio or mass ratio of α configuration to β configuration in the product.

In the present application, unless otherwise specified, when two or more materials are mixed at the same time, the order of addition may be adjusted according to the operating habits of those skilled in the art. Specifically, for example, "add a crude compound of formula II to solvent D" includes but it is not limited to the following mixing schemes: "add a crude compound of formula II to solvent D", "add solvent D to a crude compound of formula II" or "add solvent D and a crude compound of formula II at the same time and mix them."

In the present application, the compound of formula III may be prepared by referring to the prior art (including but not limited to the document Org Process Res Dev. 2002; 6(6):847-50), or may be prepared according to the method provided in examples of the present application.

DETAILED DESCRIPTION

The following examples are used to further explain the present application, but it does not constitute a restriction or limitation to the present application. Unless otherwise specified, reagents used in the examples are all commercially available.

Example 1 Preparation of Compound of Formula III-1

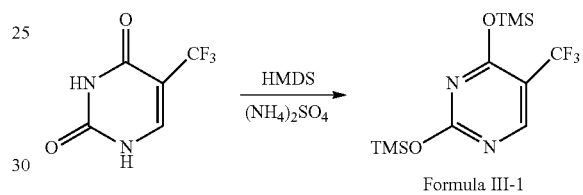

Formula III-1

Under the protection of nitrogen, pre-dried acetonitrile (42 kg), 5-trifluoromethyluracil (18 kg), HMDS (19.8 kg) and ammonium sulfate (796 g) were added into a 200 L reactor. The temperature of material liquid was controlled at 75° C. to 85° C., and the reaction was stirred for 4 h, then stopped. The temperature of the material liquid was firstly controlled at 45° C. to 55° C. to concentrate under reduced pressure to remove acetonitrile. Then it was heated to 65° C. to 75° C. to continue to concentrate under reduced pressure to remove excess HMDS. After concentration, 13.1 kg of anisole was added to the residue to dissolve it, filtered, and the filtrate was collected to afford 44.3 kg of anisole solution containing the compound of formula III-1 (wherein, the mass of the compound of formula III-1 was 31.2 kg, the mass of anisole was 13.1 kg).

Example 2 Preparation of Compound of Formula II-1

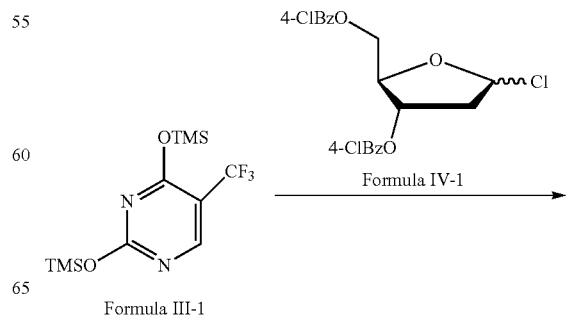

Formula III-1     Formula IV-1

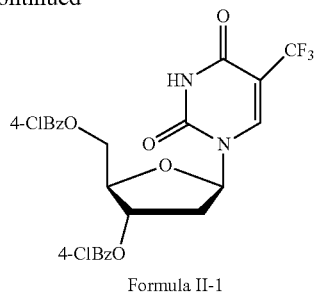

Formula II-1

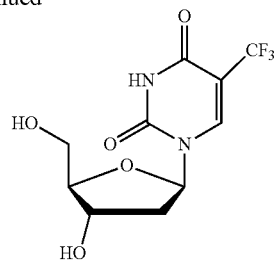

Formula I

Under the protection of nitrogen, acetic anhydride (1.96 kg) was added to the solution of anisole containing the compound of formula III-1 prepared in Example 1. The system temperature was raised to 40° C. to 50° C. Under stirring, compound of formula IV-1 was added in 5 batches (9.5 kg*5, α/β is about 60:40), with one batch per 0.5 h. After the compound of formula IV-1 was added, the reaction was continued to stir for 2 to 3 h at a controlled temperature of 40° C. to 50° C. After consumption of the compound of formula III-1 monitored by thin layer chromatography, the reaction was stopped, and the reaction system was syrupy and easy to stir.

74 kg of absolute ethanol was added to the reaction system, and the solid was dispersed uniformly by stirring. The system was crystallized at −5 to 5° C. for 7 h to 10 h, and the filter cake was air-dried at 45° C. to 55° C. for 14 to 18 h to obtain 46.72 kg crude compound of formula II-1. (α:β0=1:14.1)

654 kg of absolute ethanol was pumped into a 1000 L glass-lined reactor, and 46.72 kg of crude compound of formula II-1 prepared in the previous step was added. It was heated to 75° C. to 85° C. and stirred to clear, then cooled to 20° C. to 25° C., filtered, and the filter cake was air-dried at 45° C.-55° C. for 6 to 8 h to afford 33.88 kg of refined product of formula II-1 compound (a: =0.1:99.38).

Example 3 Preparation of Trifluridine

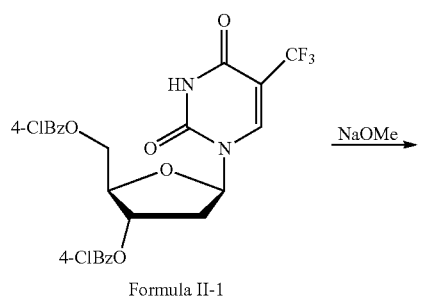

Formula II-1

Under the protection of nitrogen, 160 kg of anhydrous methanol and 23.2 kg of refined product of formula II-1 were added into a 300 L reactor, and it was stirred at a controlled system temperature of −20° C. to −10° C. cooled with chilled water. The pre-prepared methanol solution of sodium methoxide was added dropwise (5.57 kg sodium methoxide, 26 kg methanol). After addition, maintaining the temperature, the reaction was stirred for another 2 h. After consumption of the refined product of formula II-1 monitored by thin layer chromatography, controlling the temperature at −20° C. to −10° C., acetic acid was added dropwise to adjust the pH of system to neutral.

The resulting reaction solution was concentrated to dryness under reduced pressure at 35° C. to 45° C. 150 kg of acetone was added to the concentrate under stirring. It was stirred for 1 h, filtered, and the filtrate was concentrated to dryness at 30° C. to 40° C. The residue was slurried twice with 50 kg ethyl acetate, filtered, and the filter cake was air-dried at 45° C. to 55° C. for 6 h to afford 9.4 kg of crude trifluridine.

Preheated purified water (27.6 kg) firstly to 75° C. to 85° C., added 9.2 kg of the crude trifluridine prepared in the previous step under stirring until to dissolve, and then filtered. The filtrate was cooled to 0° C. to 5° C., and stirred for crystallization for 10 h, filtered. The filter cake was air-dried at 45° C. to 55° C. for 10 h to 14 h to afford 7.3 kg of refined product trifluridine.

Example 4 Preparation of Compound of Formula II-1

The compound of formula II-1 was prepared using the types of acids with feed ratios shown in Table 1, referring to the preparation method similar to Example 2, and the ratio of α:β was determined.

Unless otherwise specified, the types of other raw materials, solvents and their mutual ratios not shown in Table 1 all adopt those raw materials, solvents and ratios described in Example 2.

TABLE 1

| | Feeding | | | | α:β (mol:mol) | | Yield (%) |
|---|---|---|---|---|---|---|---|
| Acids | Acid/Compound of formula III-1 (eq) | amount of compound of formula III-1 (g) | Properties of reaction system | | End of reaction system | Crude compound of formula II-1 | Crude compound of formula II-1 |
| No | — | 120 | The system is doughy and not easy to stir | | 1:1.7 | 1:1.8 | 85 |
| Acetic anhydride | 0.2 | 120 | The system is syrupy and easy to stir | | 1:5.35 | 1:14.1 | 80 |
| | 0.1 | 120 | | | 1:4.5 | 1:6.3 | 67 |
| | 0.2 | 7.9 | | | 1:5.4 | 1:10.3 | 75 |

TABLE 1-continued

| Acids | Acid/Compound of formula III-1 (eq) | Feeding amount of compound of formula III-1 (g) | Properties of reaction system | End of reaction system | α:β (mol:mol) Crude compound of formula II-1 | Yield (%) Crude compound of formula II-1 |
|---|---|---|---|---|---|---|
| | 0.1 | 7.9 | | 1:4.9 | 1:6.3 | 82 |
| | 0.05 | 7.9 | | 1:4.75 | 1:6.2 | 81 |
| Acetic acid | 0.05 | 120 | The system is syrupy and easy to stir | 1:2.57 | 1:2.74 | 70 |
| | 0.1 | 7.9 | | 1:5.38 | 1:4.9 | 69 |
| | 0.05 | 7.9 | | 1:4.4 | 1:4.4 | 88 |
| HCl/Isopropanol (6M/L) | 0.1 | 7.9 | The system is syrupy and easy to stir | 1:5.96 | 1:4.64 | 74 |

What is claimed:

1. A method for preparing a compound of formula II, wherein a compound of formula III and a compound of formula IV are reacted in a first solvent in the presence of an acid to obtain the compound of formula II,

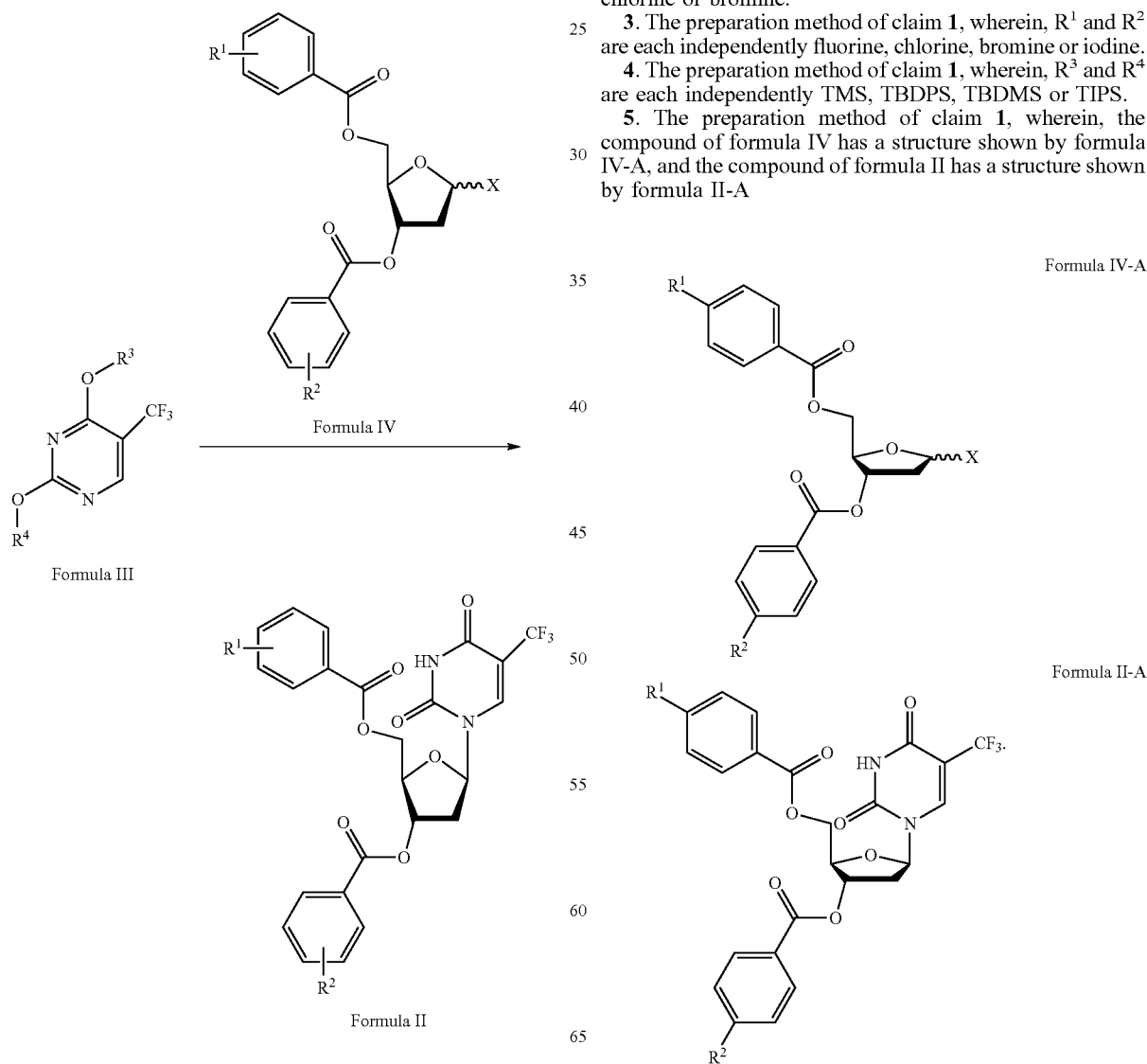

Formula III

Formula IV

Formula II

Formula IV-A

Formula II-A wherein, X is a halogen atom;
$R^1$ and $R^2$ are each independently hydrogen, methyl or halogen atoms;
$R^3$ and $R^4$ are hydroxyl protecting groups; and
the acid is one or a mixture of two or more of HCl, formic acid, acetic acid, or acetic anhydride.

2. The preparation method of claim 1, wherein, X is chlorine or bromine.

3. The preparation method of claim 1, wherein, $R^1$ and $R^2$ are each independently fluorine, chlorine, bromine or iodine.

4. The preparation method of claim 1, wherein, $R^3$ and $R^4$ are each independently TMS, TBDPS, TBDMS or TIPS.

5. The preparation method of claim 1, wherein, the compound of formula IV has a structure shown by formula IV-A, and the compound of formula II has a structure shown by formula II-A 6. The preparation method of claim 1, wherein, the compound of formula IV has a structure shown by formula IV-1, the compound of formula III has a structure shown by formula III-1, and the compound of formula II has a structure shown by formula II-1:

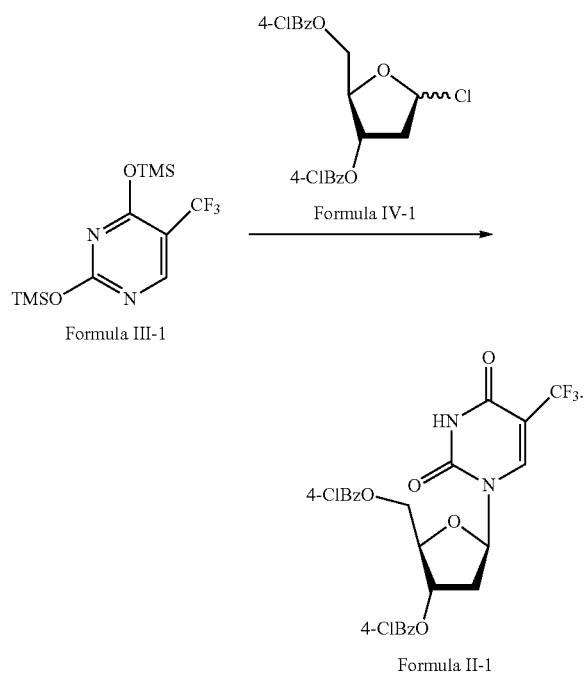

7. The preparation method of claim 1, wherein, the molar ratio of the compound of formula III to the compound of formula IV is 1:1 to 1:3.

8. The preparation method of claim 1, wherein, the acid is one or a mixture of two or more of an alcohol solution of hydrogen chloride, formic acid, acetic acid, or acetic anhydride.

9. The preparation method of claim 1, wherein, the molar ratio of the acid to the compound of formula III is 0.05:1 to 0.3:1.

10. The preparation method of claim 1, wherein, the first solvent is one or a mixture of two or more of 1,2,4-trichlorobenzene, o-dichlorobenzene, chlorobenzene, anisole, toluene, nitrobenzene, isopropyl alcohol, ether, tetrahydrofuran, and ethyl acetate.

11. The preparation method of claim 1, wherein, the ratio of the mass of the first solvent to the mass of the compound of formula III is 0.35:1 to 0.77:1.

12. The preparation method of claim 1, wherein, the method further comprises: adding solvent B to the reaction system which contains the compound of formula II after reacting, and cooling for crystallization to obtain a preliminarily purified compound of formula II, wherein the solvent B is one or a mixed solvent of two or more of ethanol, isopropanol, and n-propanol.

13. The preparation method of claim 12, wherein, the method further comprises: dissolving the compound of formula II purified preliminarily in a solvent D, and cooling for crystallization to obtain a refined product of the compound of formula II; wherein, the solvent D is one or a mixed solvent of two or more of ethanol, isopropanol, and n-propanol.

14. A method for preparing trifluridine, wherein, the method comprises:
obtaining the compound of formula II according to the method of claim 1;
dissolving the compound of formula II in anhydrous methanol to obtain its anhydrous methanol solution;
adding a methanol solution of sodium methoxide to the anhydrous methanol solution of the compound of formula II for reacting to obtain trifluridine

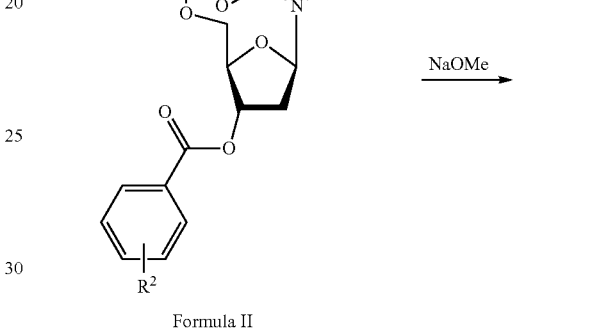

15. The preparation method of claim 7, wherein, the molar ratio of the compound of formula III to the compound of formula IV is 1:1.1 to 1:1.2.

16. The preparation method of claim 9, wherein, the molar ratio of the acid to the compound of formula III is 0.15:1 to 0.2:1.

17. The preparation method of claim 11, wherein, the ratio of the mass of the first solvent to the mass of the compound of formula III is 0.40:1 to 0.45:1.

18. The preparation method of claim 12, wherein the ratio of the mass of the solvent B to the mass of the compound of formula III is 1.5 to 4:1.

19. The preparation method of claim 13, wherein, the ratio of the mass of the solvent D to the mass of the compound of formula II purified preliminarily is 7.9:1 to 20:1.

* * * * *